United States Patent [19]

Chess et al.

[11] Patent Number: 5,674,456
[45] Date of Patent: Oct. 7, 1997

[54] MEDICAL SPECIMEN SHIPPING CONTAINER

[75] Inventors: Quintus Chess, 1495 Pine Knoll La., Mamaroneck, N.Y. 10543; Joseph Z. Eisner, New York; Henry C. Oksman, Mamaroneck, both of N.Y.

[73] Assignee: Quintus Chess, Mamaroneck, N.Y.

[21] Appl. No.: 945,046

[22] Filed: Sep. 15, 1992

[51] Int. Cl.⁶ .................................................. B01L 3/00
[52] U.S. Cl. .................... 422/102; 422/104; 422/61; 206/456; 206/564
[58] Field of Search ............................ 422/61, 102, 104; 206/438, 456, 564, 570, 571, 572

[56] References Cited

U.S. PATENT DOCUMENTS

| | | | |
|---|---|---|---|
| 3,013,656 | 12/1961 | Murphy | 206/572 |
| 3,063,549 | 11/1962 | Weichselbaum | 206/456 |
| 3,582,285 | 6/1971 | Hamilton | 422/61 X |
| 3,713,779 | 1/1973 | Sirago et al. | 422/61 X |
| 3,849,256 | 11/1974 | Linder | 422/102 X |
| 4,077,846 | 3/1978 | Hedges | 206/456 X |
| 4,595,102 | 6/1986 | Cianci et al. | 206/572 |
| 4,617,278 | 10/1986 | Reed | 422/61 X |
| 4,635,790 | 1/1987 | Jackson et al. | 206/210 |
| 4,675,286 | 6/1987 | Calenoff | 436/177 X |
| 4,706,839 | 11/1987 | Spence | 206/438 X |
| 4,713,219 | 12/1987 | Gerken et al. | 422/102 |
| 4,736,850 | 4/1988 | Bowman et al. | 206/438 X |
| 4,771,005 | 9/1988 | Spiro | 422/61 X |
| 4,782,942 | 11/1988 | Ashley et al. | 206/5.1 |
| 4,851,510 | 7/1989 | Khan | 435/543 X |
| 4,874,102 | 10/1989 | Jessop et al. | 422/102 X |
| 4,953,741 | 9/1990 | Jessop et al. | 220/273 |
| 4,960,224 | 10/1990 | Boenisch | 206/456 |
| 5,021,218 | 6/1991 | Davis et al. | 422/104 |
| 5,031,768 | 7/1991 | Fischer | 206/370 |
| 5,100,621 | 3/1992 | Berke et al. | 422/61 |
| 5,116,734 | 5/1992 | Higgs et al. | 435/28 |
| 5,149,506 | 9/1992 | Skiba et al. | 422/102 |
| 5,203,450 | 4/1993 | Benetti | 206/63.5 |

*Primary Examiner*—Harold Y. Pyon
*Attorney, Agent, or Firm*—Brown Raysman Millstein Felder & Steiner LLP

[57] ABSTRACT

A transportable container for a medical specimen, preferably in the form of a Coplin jar. The container includes a jar molded from a thermoplastic material having an open top, with the lid hingedly coupled to the top of the jar for movement between open and closed positions. The top of the jar includes a rim projecting upwardly therefrom, with the lid having a recessed inside surface including a sealing ring therein shaped like the projecting rim. The sealing ring contacts the rim and seals thereagainst when the lid is closed. A snap lock latch is coupled to the lid and releaseably snap locks to a keeper on the jar to positively lock the lid to the jar to prevent leaks. The container can be used with a kit which includes a tray which receives the container in sideways fashion only.

18 Claims, 4 Drawing Sheets

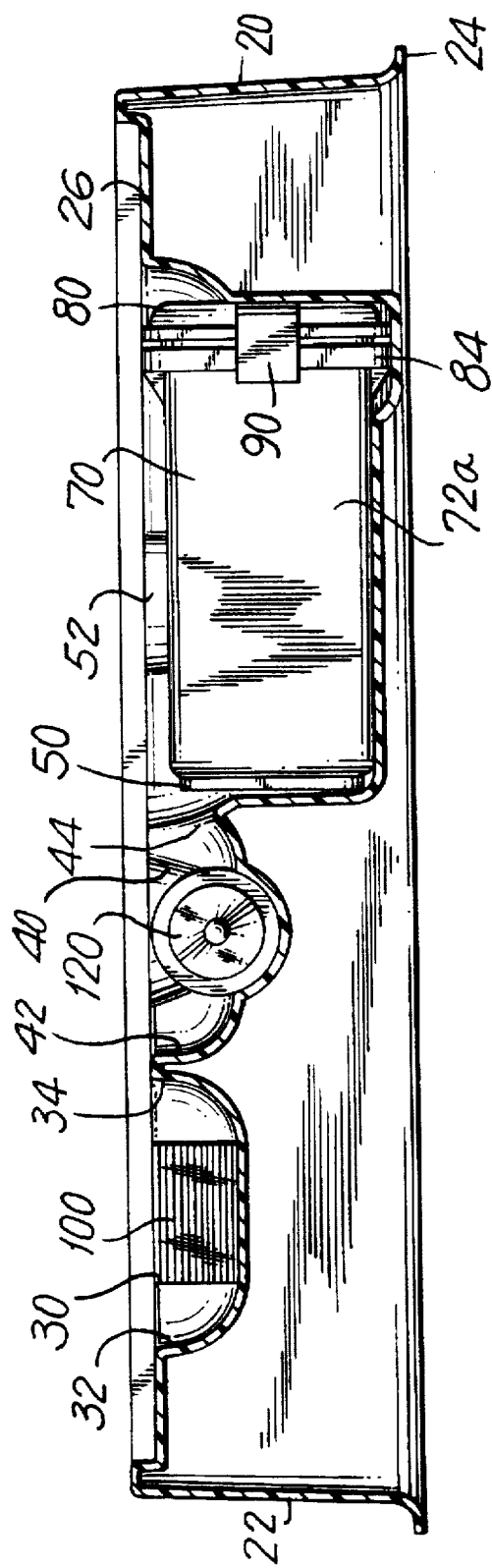
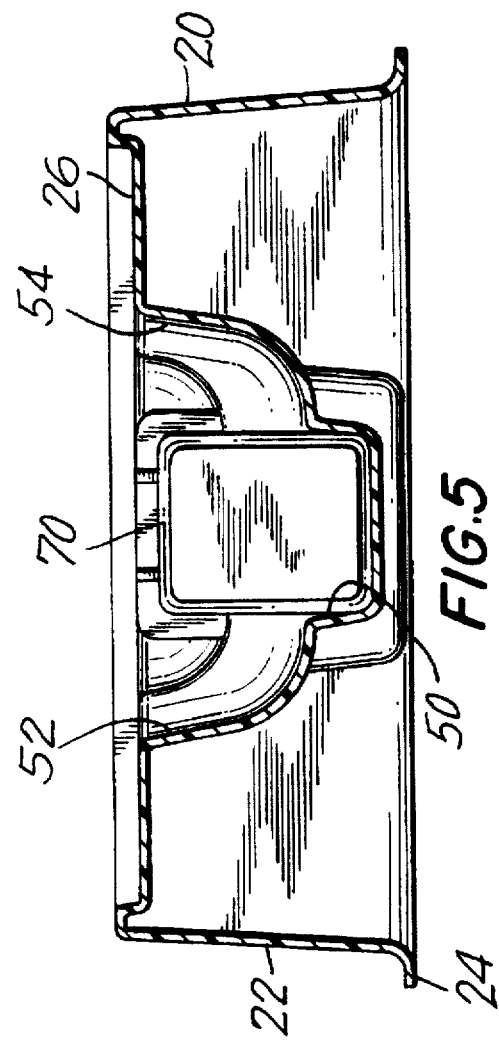

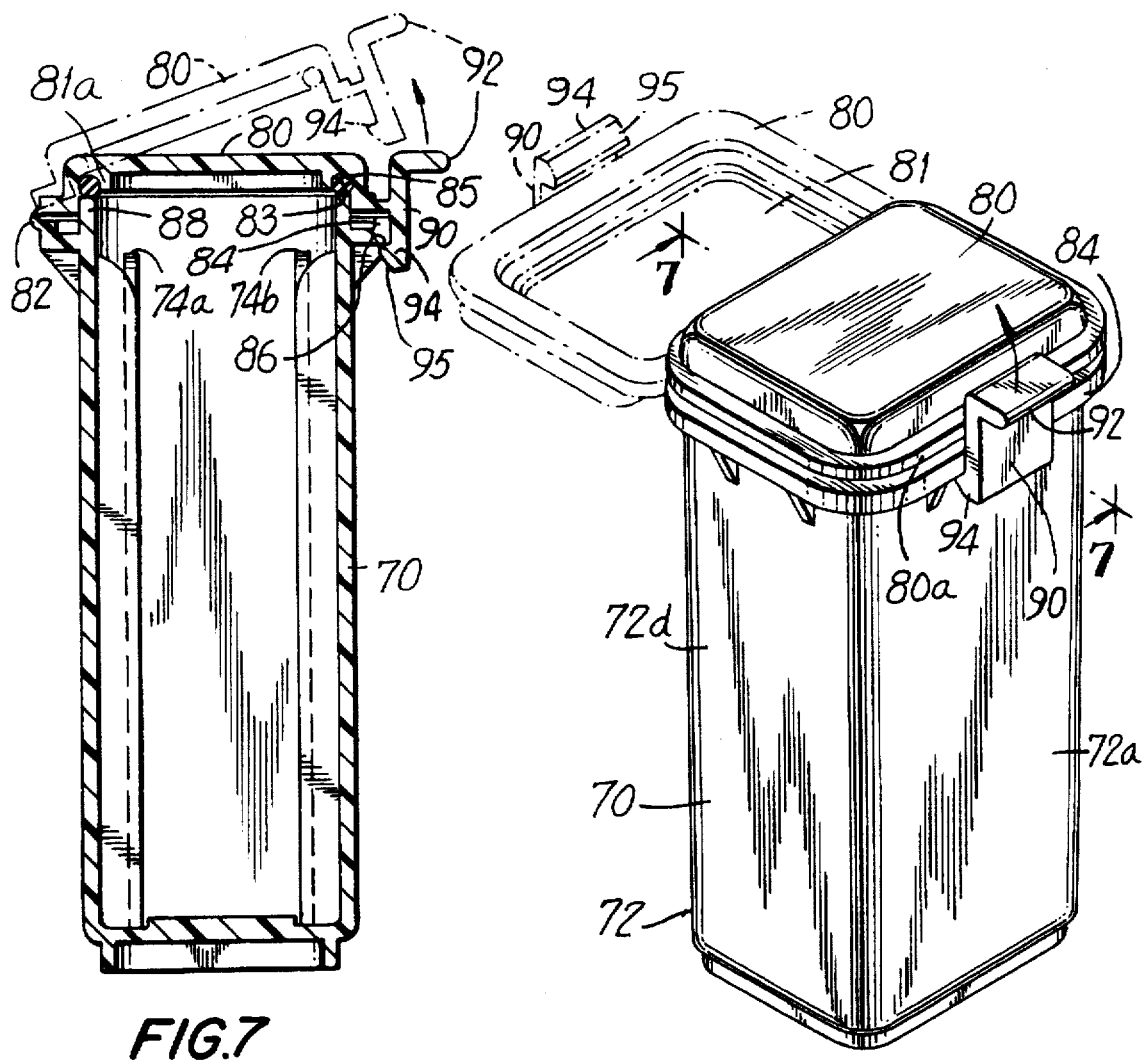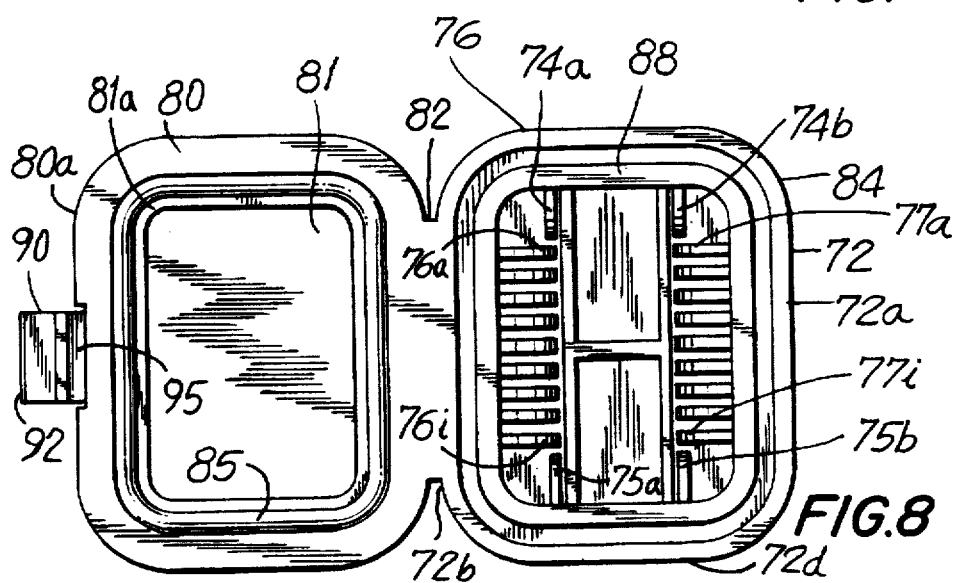

MEDICAL SPECIMEN SHIPPING CONTAINER

BACKGROUND OF THE INVENTION

The present invention is directed generally to a medical specimen shipping container and, in particular, to a specially designed Coplin jar and shipping kit which allows for the transport by regular overnight courier of medical specimens on slides in an appropriate liquid, without leaking.

Fine needle aspiration biopsy is a relatively simple test for obtaining a sample of a tumor for cytologic study and diagnosis. The test was developed in around the 1930's in New York City. The test permits surgeons to obtain a preoperative diagnosis without violating the integrity of the tumor capsule or associated tissue planes. This is important to prevent local recurrence of malignant neoplasms. While the test had been widely used in Europe, it did not become popular in the United States until recently.

This development was stimulated by the need for a cost-effective, relatively pain-free and highly accurate cancer diagnostic test. However, until recently, the test has not been utilized as much as it might because of the limited number of appropriately trained cytopathologists capable of interpretation of the very small samples obtained using the test.

During the past decade, there have been dramatic improvements in the ability of cytopathologists to render accurate diagnosis on material obtained by fine needle aspiration biopsy. Fine need aspiration biopsy specimens are stained by the Papanicolaou technique, which requires "wet-fixed" cell smears. Wet fixation is accomplished by immediate immersion of smeared cell samples on slides into a 95% ethanol solution.

This immersion is generally accomplished in a Coplin jar which has been a standard laboratory apparatus for many years. A Coplin jar generally is a square jar about the size of standard microscope slides with internal ribs which keep the slides from contacting one another after immersion in the fixative fluid. While conventional Coplin jars allowed for immersion in a fixative fluid, they did not provide an appropriate sealing system for preventing leakage of the fluid during transport. Hence, conventional Coplin jars had screw-on tops which prevented leak-proof closure in many cases.

Because of the problems with leaking Coplin jars and the inability to transport over longer distances, it proved necessary to perform such fine needle aspiration biopsy in the laboratory or hospital premises where the specimen could be examined immediately. This proved at odds with the very simplicity of fine needle aspiration biopsy which allows for the procedure to be performed in doctor's offices. Specimens obtained by a doctor in his office using fine needle aspiration biopsy, after wet fixation, could be shipped by a regular commercial courier to an appropriate laboratory for analysis only if such a transport system were available. However, appropriate leak proof Coplin jars and related shipping kits were unknown and unavailable in the art.

Accordingly, it is desired to provide a medical specimen shipping container with a leak proof jar adapted to receive slides which permits the transportation of medical specimens through appropriate overnight courier services such as Federal Express or the like.

SUMMARY OF THE INVENTION

Generally speaking, in accordance with the present invention, a transportable container for a medical specimen and a medical specimen transport kit using the transportable container, are provided. The transportable container includes a jar having an open top molded from a thermoplastic material with a lid hingedly coupled to the top of the jar for movement between open and closed positions. The top of the jar includes a rim projecting upwardly therefrom, with the lid having a recessed inside surface including a sealing ring therein shaped like the projecting rim. The sealing ring contacts the rim and seals thereagainst when the lid is closed. A snap lock latch is coupled to the lid and releasably snap locks to a keeper on the jar to positively lock the lid to the jar to prevent leaking.

Preferably, the jar is a Coplin jar having slots for holding slides therein. The jar is preferably integrally formed with a living hinge coupling the lid to the jar.

The kit includes a tray preferably formed from a plastic blow molded material which includes at least one recessed portion for receiving the Coplin jar. The Coplin jar is generally rectangular in shape such that the front of the jar where the latch appears and the back are wider than the opposing sides thereof. The recessed portion in the tray is only essentially as wide as the opposing sides of the jar so that the jar can only be inserted sideways in the recessed portion. An enlarged depression formed as part of the recessed portion receives the lid and latch of the jar to prevent inadvertent contact of the latch to keep the jar closed during transport.

The tray may include other recessed portions for holding a plurality of slides and a tube for containing appropriate fluid.

Shipment of a medical biopsy specimen from a patient to any desired laboratory for analysis by overnight or other regular commercial courier can now be achieved under the present method. The method includes obtaining the specimen from the patient and applying the specimen to a slide. The slide is inserted in a prefilled Coplin jar for wet fixation. The Coplin jar is then sealed to prevent leaking and the jar is shipped by commercial courier to a laboratory for analysis.

Accordingly, it is an object of the present invention to provide a leak-proof, transportable Coplin jar.

Another object of the present invention is to provide a leak-proof Coplin jar which is suitable for shipping by regular overnight courier services.

Yet another object of the present invention is to provide a medical specimen transport kit which permits doctors to perform fine needle aspiration biopsy in their offices and thereafter permits safe and secure shipment of the biopsy specimen to any desired laboratories, cytopathologists or pathologists for testing.

Still a further object of the present invention is to provide a specially designed Coplin jar which is leak-proof and transportable and especially adapted for use in fine needle aspiration biopsy.

Yet still another object of the present invention is to provide a method of shipping a medical specimen under wet fixation using a regular commercial courier.

Still other objects and advantages of the invention will in part be obvious and will in part be apparent from the specification.

The invention accordingly comprises the several steps and the relation of one or more of such steps with respect to each of the others, and the apparatus embodying features of construction, combination of elements and arrangement of parts which are adapted to effect such steps, all as exemplified in the following detailed disclosure, and the scope of the invention will be indicated in the claims.

BRIEF DESCRIPTION OF THE DRAWINGS

For a fuller understanding of the invention, reference is had to the following description taken in connection with the accompanying drawings, in which:

FIG. 4 is a sectional view taken along line 4—4 of FIG. 3;

FIG. 5 is a sectional view taken along line 5—5 of FIG. 3;

FIG. 6 is a perspective view of a Coplin jar used in the shipping container of the present invention, shown with the top closed, and opened in phantom;

FIG. 7 is a sectional view taken along line 7—7 of FIG. 6; and

FIG. 8 is a top plan view of the Coplin jar in FIG. 6 shown with the top thereof in open condition.

DETAILED DESCRIPTION OF THE PREFERRED EMBODIMENTS

Figure 1:
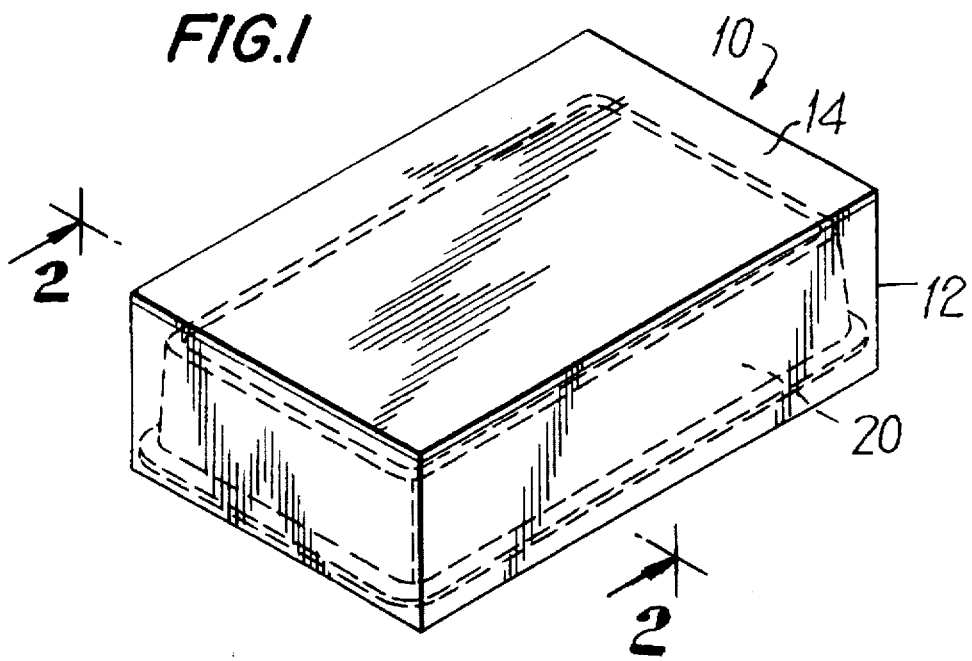
FIG. 1 is a perspective view of a medical specimen shipping container constructed in accordance with a preferred embodiment of the present invention.
Figure 2:
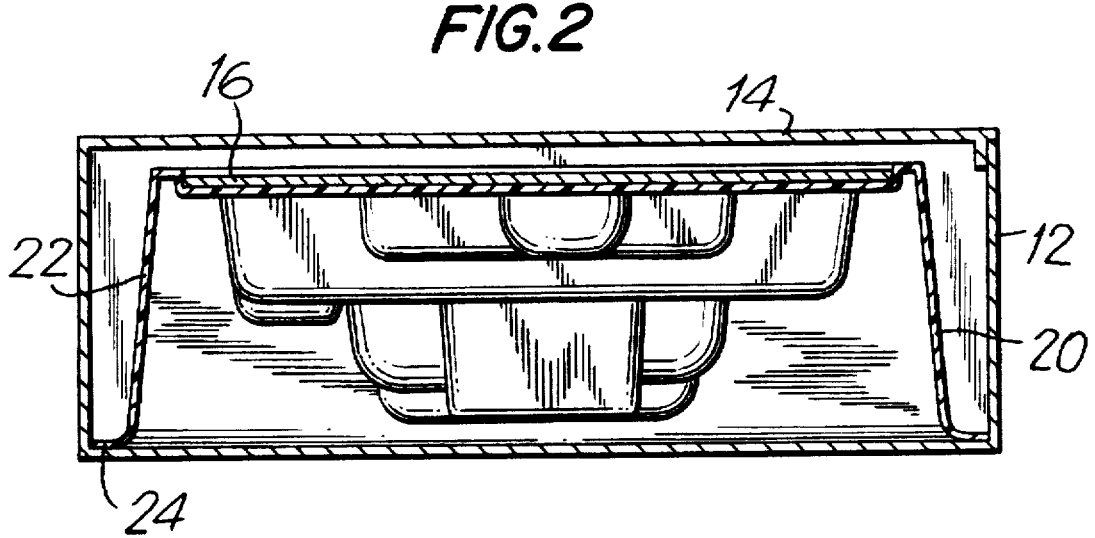
FIG. 2 is an enlarged sectional view taken along line 2—2 of FIG. 1.

Reference is first made to FIGS. 1 and 2 of the drawings which depict a medical specimen shipping container, generally indicated at 10, which includes an outer corrugated cardboard box 12 and an inner plastic tray 20. Box 12 preferably includes a top 14 which can be opened to permit access to tray 20. Literature 16 is found at the top of tray 20, and may provide use and shipping instructions and other information to the doctor.

Figure 3:
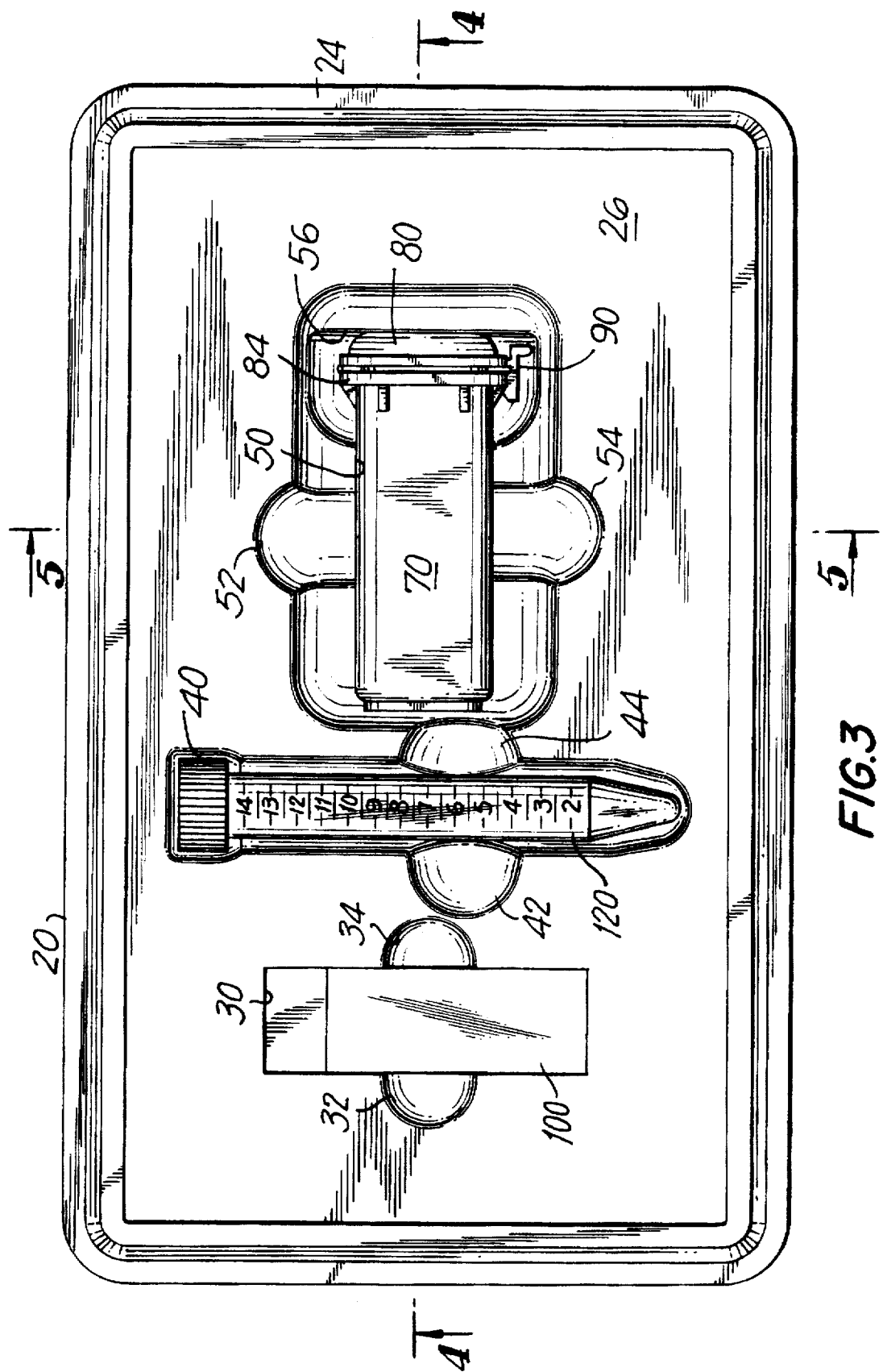
FIG. 3 is a top plan view of the container insert tray and various components of the kit.

Referring now additionally to FIGS. 3 through 5, it is noted that tray 20 is preferably formed from a plastic blow-molded material in the form and shape depicted. Tray 20 includes a depending skirt 22 therearound which terminates in a foot 24. Upper surface 26 of tray 20 is recessed somewhat as depicted and defines three separate recessed regions 30, 40 and 50.

Recessed region 30 is rectangular in shape as depicted and is adapted to receive a plurality of glass microscope slides 100. Opposing finger depressions 32 and 34 on opposite sides of slides 100 allow finger access to the slides. In a preferred embodiment, ten slides are provided.

Second recessed region 40 is shaped to receive a standard centrifuge tube 120 filled with an appropriate liquid. Finger depressions 42 and 44 are formed on opposite sides of tube 120 to permit ready access thereto and removal of the tube 120 from tray 20. In a preferred embodiment for fine needle aspiration biopsy, centrifuge tube 120 is filled with seven milliliters of a 50% ethanol solution (reagent grade).

Third recessed region 50 is adapted to receive a specially designed and constructed Coplin jar 70, the details of construction of which will be described below in detail with reference to FIGS. 6 through 8. Recessed region 50 also includes opposed finger depressions 52 and 54 to permit access and removal of Coplin jar 70 as explained below in detail.

Referring now additionally to FIGS. 6 through 8, it is seen that Coplin jar 70, which is preferably formed from a thermoplastic material, includes a body or container portion 72 and a cap or lid 80 hingedly secured thereto, preferably through a living hinge 82. It is noted that container 72 is rectangular in cross section and includes wider front and rear surfaces 72a and 72b than opposing side surfaces 72c and 72d. A lip 84 projects outwardly from body 72 therearound and defines a ledge or keeper 86 best depicted in FIG. 7.

A pivotable latch 90 is integrally, pivotably formed with cap 80 on the front 80a thereof and includes a first end having a finger projection 92 and a second end having a latch projection 94 which is releaseably captured against and under ledge 86 of lip 84 when cap 80 is closed. It is noted that latch projection 94 includes a beveled surface 95 which rides against lip 84 as cap 80 is being closed. Thereafter, latch projection 94 will snap lock under ledge 86 due to the resiliency of the integral molding.

An inset shoulder 88 extends upwardly beyond lip 84. Cap 80 includes an internal recessed region 81 including a rib 81a which defines a channel 83. Channel 83 is sized to receive and hold a gasket 85 in the form of a resilient O-ring. As best depicted in FIG. 7, when cap 80 is snapped shut and latch 90 is engaged under ledge 86, O-ring 85 will press against shoulder 88 to seal off the inside of Coplin jar 70 to prevent any leaks of liquid therein.

This construction provides a positive snap locking of Coplin jar 70 when cap 80 is closed. Gasket 85 will be forced against shoulder 86 to seal off the container and no further tightening is required to prevent leaks.

Internally, Coplin jar 70 includes opposing spaced ribs 74a and 74b on one side thereof and similar ribs 75a and 75b on the other side thereof. The inner front and back surfaces 72a and 72b of body 72 include opposing ribs 76a through 76i and 77a through 77i, respectively. As best depicted in FIG. 7, the upper edge of each of these ribs is curved. The ribs are spaced to permit only one glass slide 100 to fit therebetween and to prevent angled insertion of the slides. Accordingly, the ribs permit only one glass slide to be included in each opposing slot. This will prevent contact of adjacent slides. In a preferred embodiment, ten slide receiving positions are provided. The Coplin jar is prefilled with a clear 95% ethanol solution (reagent grade) in an amount sufficient to cover a single slide, but not too much which prevents overflow if ten slides are used.

In a preferred embodiment, Coplin jar 70 will be about 82 mm deep and have bottom cross-section dimensions of 26.5×31.0 mm and top cross-section dimensions of 28.0× 32.5 mm. The internal slide ribs are about 1.5 mm thick and are spaced to provide a slot width of between about 1.5–1.7 mm. The ribs are preferably angled at the top about 30° to allow easy capture of the slides as they are inserted.

As noted above, third recessed region 50 in tray 20 supports Coplin jar 70 therein. The width of recessed region 50 is essentially the same or slightly larger than the width of opposing sides 72c and 72d of jar 70 so that jar 70 can only be placed sideways in recessed region 50 as best depicted in FIGS. 3 through 5. Accordingly, latch 90 will face sideways when jar 70 is supported in the tray.

Recessed region 50 includes an enlarged recessed area 56 at one end thereof adapted to receive and accommodate the enlarged area of lid 80, lip 84 and latch 90. As aforenoted, with this configuration, Coplin jar 70 can only be placed sideways in recessed region 50, as depicted. Thus, latch 90 is recessed in the depressed area and cannot be inadvertently disturbed during shipment of the container.

In use, the kit will be provided to the doctor as depicted in FIGS. 1 and 2. When the top of the box is opened, the relevant use and shipping instructions will be immediately available and visible to the doctor. When this literature is removed, the upper surface of the tray is exposed with the slides, tube and Coplin jar. The doctor can then perform the appropriate fine needle aspiration biopsy and place the slides with specimens in the slots in the Coplin jar, which is prefilled with the appropriate wet fixation solution. A simple pressing down of the lid against the jar causes the snap closure to lock providing a positive, leak-proof lock. The closed Coplin jar is then placed back in the tray in sideways fashion, the only way it will fit. The cardboard box is closed and then is placed in an appropriate container provided by the courier service. For example, Federal Express courier service provides a lab pack for the shipment of laboratory specimens. The present kit meets the requirements and has been approved for shipment by Federal Express in Federal Express lab packs. When the kit is received at the laboratory, appropriate testing of the specimens can occur.

Although the present kit and Coplin jar have been designed for use especially with fine needle aspiration biopsy, it is noted that since other types of cytopathology specimens require wet fixation, the such and/or kit may be used for transportation of such other specimens. An example of another such usage would be in connection with endoscopic cytology.

It will thus be seen that the objects set forth above, among those made apparent from the preceding description, are efficiently attained and, since certain changes may be made in the above construction and method without departing from the spirit and scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed is:

1. A leak-proof transportable container for a medical specimen comprising an essentially rectangular jar molded from a thermoplastic material having an open top, said jar including a front and a back, a lid having a front and a back, the back of said lid being hingedly coupled to the top of the back of said jar by a living hinge for pivotable movement between open and closed positions, said top having a rim projecting upwardly therefrom, said rim having an upper horizontal surface, said lid having a recessed inside surface including a gasket supported therein, said gasket contacting said upper horizontal surface of said rim and pressing thereagainst when said lid is closed, and snap lock closure means coupled to the front of one of said jar and said lid and releaseably snap coupleable to the front of the other of said jar and said lid, said snap lock closure means cooperating with said living hinge to positively lock said lid to said jar and said gasket against said upper horizontal surface of said rim to prevent leaks.

2. The transportable container as claimed in claim 1, wherein said jar, lid, living hinge and snap lock closure means are integrally molded from a thermoplastic material.

3. The transportable container as claimed in claim 2, wherein said jar is a Coplin jar filled with a predetermined amount of liquid solution.

4. The transportable container as claimed in claim 3, wherein said Coplin jar includes internal slots for receiving slides.

5. The transportable container as claimed in claim 4, wherein said slots are defined by opposed internal ribs on the front and back of said Coplin jar.

6. The transportable container as claimed in claim 5, wherein said Coplin jar is rectangular in cross-section.

7. The transportable container as claimed in claim 1, wherein said gasket is an O-ring.

8. The transportable container as claimed in claim 7, wherein said snap lock closure means includes a pivotable latch integrally formed on the front of said lid, the front of said jar including a keeper for releasably snap capturing said latch.

9. The transportable container as claimed in claim 8, wherein said gasket is compressed against said upper surface of said rim when said latch is coupled to said keeper.

10. A leak-proof Coplin jar for supporting slides in a liquid solution for transport comprising an elongated plastic container having an open top and slide receiving means therein for removably supporting said slides, a lid having a first edge hingedly coupled to the top of said container by a living hinge which permits said lid to pivot with respect to said top of said container, said lid including a pivotable latch on a second edge thereof opposing said first edge, said container including keeper means for releaseably capturing said latch, said lid having an inner surface facing said open top of said container, said inner surface including a gasket supported therein, said top of said container including an upper surface that presses against said gasket to seal said container when said latch is secured to said keeper, no portion of said lid extending into said container when said lid is closed.

11. The Coplin jar as claimed in claim 10, wherein said latch is integrally formed on the front of said lid.

12. The Coplin jar as claimed in claim 11, wherein said lid is integrally formed to said container through a living hinge.

13. The Coplin jar as claimed in claim 10, wherein said container is rectangular in shape and includes wider front and back surfaces than opposing side surfaces.

14. The Coplin jar as claimed in claim 13, wherein said slide receiving means include internal ribs on the front and back internal surfaces of said container.

15. The Coplin jar as claimed in claim 14, wherein said ribs include upper curved ends.

16. The Coplin jar as claimed in claim 15, wherein said ribs define slots only wide enough to receive a single slide therein.

17. The Coplin jar as claimed in claim 10, wherein said container is narrower at the bottom than at the top thereof.

18. The Coplin jar as claimed in claim 10, wherein said upper surface of said container includes a lip extending outwardly therefrom, an upstanding rim on said upper surface spaced inwardly from said lip, said rim confronting and pressing against said gasket when said lid is closed.

* * * * *